(12) United States Patent
Heim

(10) Patent No.: US 8,287,596 B1
(45) Date of Patent: Oct. 16, 2012

(54) INTRAOPERATIVE SURGICAL BARRIER AND RELATED METHODS

(75) Inventor: Stephen Heim, Warrenville, IL (US)

(73) Assignee: NuVasive, Inc., San Diego, CA (US)

( * ) Notice: Subject to any disclaimer, the term of this patent is extended or adjusted under 35 U.S.C. 154(b) by 811 days.

(21) Appl. No.: 11/974,443

(22) Filed: Oct. 11, 2007

Related U.S. Application Data

(60) Provisional application No. 60/851,185, filed on Oct. 11, 2006.

(51) Int. Cl.
*A61F 2/44* (2006.01)
*A61B 17/88* (2006.01)

(52) U.S. Cl. .................. 623/17.12; 623/17.11; 606/279

(58) Field of Classification Search .... 623/17.11–17.16; 606/246–279
See application file for complete search history.

(56) References Cited

U.S. PATENT DOCUMENTS

| | | | | |
|---|---|---|---|---|
| 4,753,637 | A * | 6/1988 | Horneffer | 604/509 |
| 2004/0138703 | A1 * | 7/2004 | Alleyne | 606/213 |
| 2004/0157798 | A1 * | 8/2004 | Little | 514/89 |
| 2004/0186576 | A1 * | 9/2004 | Biscup et al. | 623/17.12 |
| 2005/0234557 | A1 * | 10/2005 | Lambrecht et al. | 623/17.16 |
| 2006/0206209 | A1 * | 9/2006 | Cragg et al. | 623/17.16 |

* cited by examiner

*Primary Examiner* — Eduardo C Robert
*Assistant Examiner* — Nicholas Plionis
(74) *Attorney, Agent, or Firm* — Jonathan Spangler; Heather Prado

(57) ABSTRACT

A surgical barrier to be introduced during spinal fusion surgery in order to protect a specified area of the patient from adverse effects associated with surgical techniques. A method of using the surgical barrier including: establishing an operative corridor to a target surgical site; introducing a spinal fusion implant into the through said operative corridor, the fusion implant including fusion-enhancing material; introducing at least a portion of an intraoperative surgical barrier through the operative corridor to the surgical target site, the intraoperative surgical barrier including an expandable seal member; and expanding the expandable seal member to establish a barrier between the fusion implant and at least a portion of the surgical target site and the operative corridor.

5 Claims, 8 Drawing Sheets

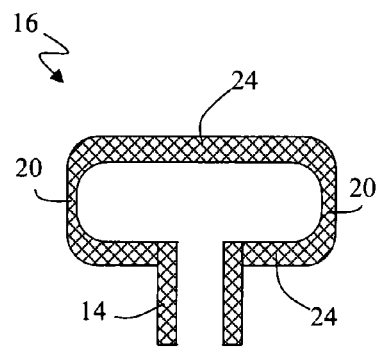
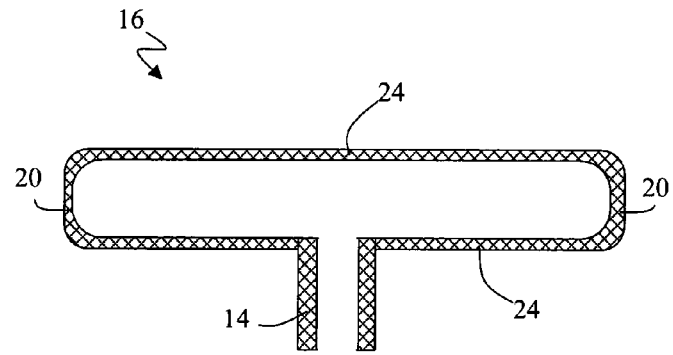
FIG. 5  FIG. 6
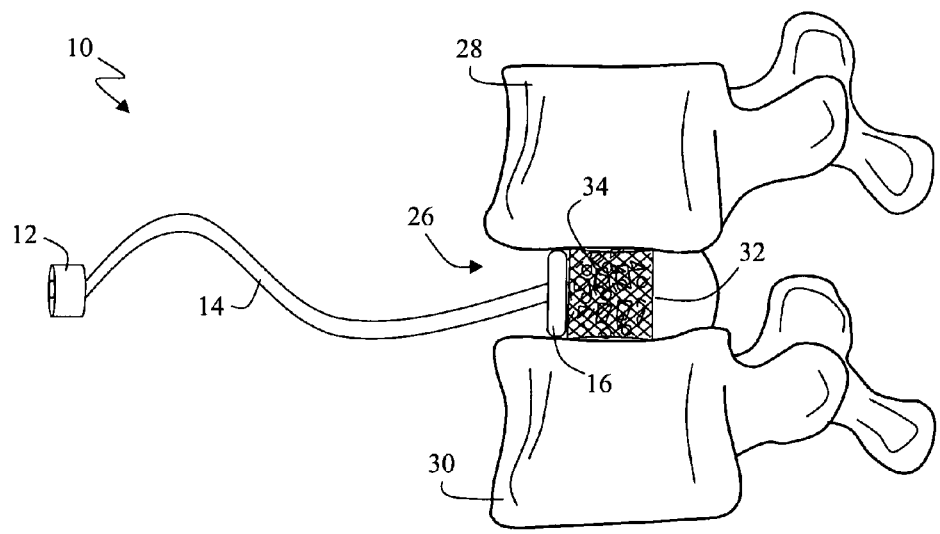
FIG. 7

INTRAOPERATIVE SURGICAL BARRIER AND RELATED METHODS

CROSS-REFERENCES TO RELATED APPLICATIONS

The present non-provisional patent application claims the benefit of priority from commonly owned and co-pending U.S. Provisional Patent Application Ser. No. 60/851,185, entitled "Intraoperative Surgical Barrier," filed on Oct. 11, 2006, the entire contents of which are hereby expressly incorporated by reference into this disclosure as if set forth fully herein.

BACKGROUND OF THE INVENTION

I. Field of the Invention

The present invention relates generally to spinal surgery and, more particularly, to a method and device for protecting a surgical site from adverse effects during operative wound irrigation.

II. Discussion of the Prior Art

Currently there are nearly 500,000 spine lumbar and cervical fusion procedures performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Introducing the intervertebral implant serves to restore the height between adjacent vertebrae ("disc height"), which reduces if not eliminates neural impingement commonly associated with a damaged or diseased disc. Distraction of the disc space with subsequent decompression of nerve roots can be accomplished by inserting such a device between the adjacent vertebrae.

Current spinal fusion implants utilize grafts of either bone or artificial implants to fill the intervertebral disc space. Spinal fusion implants or grafts may be made of metal, plastic composites, ceramics, or bone. Natural bone grafts have also been developed including autologous and allograft bone grafts. Other bone grafts may include certain man-made substances including binder joining bone chips and composite bone structures.

Often these spinal implants are accompanied by bone morphogenic proteins (BMPs) which serve to enhance fusion of the two vertebrae. BMPs are highly effective growth factors, in that they promote the formation of new bone and the fusion of existing bone. A primary drawback to the use of BMPs is a generally high, and sometimes prohibitive, cost associated therewith. As such, surgeons seek to be cautious with BMP use, so as not to waste the costly proteins.

A common problem with BMP use in spinal fusion is the loss of BMP during irrigation of the surgical site. Irrigation of the operative wound is a standard operative technique, and is vital for the prevention of peri-operative infection. Thus surgeons are often left with the difficult choice of irrigating the surgical site, and thus risking the loss of expensive BMP and lessening the efficacy of the spinal fusion, or not irrigating the site and risking infection.

Thus a need remains for a device which can facilitate the irrigation of the operative wound, while preserving the integrity and precise location of BMP. The present invention is directed at solving this problem.

SUMMARY OF THE INVENTION

The present invention addresses this problem by providing an inflatable intra-operative barrier which protects the spinal fusion site, and thus the BMP, from dilution or disruption during irrigation. The barrier facilitates proper irrigation of the operative wound by providing a temporary waterproof seal which prevents the irrigating fluid (including but not limited to water, air, or saline) from disrupting or diluting the BMP. The intra-operative surgical barrier of the present invention may be comprised of any suitable flexible material, including but not limited to silicone, rubber/latex, polyvinyl chloride, or any combination of these materials. The intra-operative surgical barrier of the present invention may be provided in any number of suitable shapes and sizes depending upon the particular surgical procedure or need. The barrier may be used in various regions of the spine, and from various approach angles (ie. posterior, anterior, lateral, transverse or off-midline posterior, etc.) without departing from the scope of the present invention.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 5 is a cross-sectional view of the deflated surgical barrier of FIG. 1;

FIG. 6 is a cross-sectional view of the inflated surgical barrier of FIG. 2;

FIGS. 7-8 are side and top views, respectively, of the inflated surgical barrier of FIG. 2 applied within an intervertebral space from an anterior aspect of the spine, illustrating one example of use according to the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The intra-operative surgical barrier disclosed herein boasts a variety of inventive features and components that warrant patent protection, both individually and in combination.

FIGS. 1-4 illustrate an intra-operative surgical barrier 10 according to a first broad aspect of the present invention. The surgical barrier 10 of the present invention includes a valve unit 12, tubing 14, and an inflatable seal 16. The surgical barrier 10 may be provided with varying length and width dimensions, for both the tubing 14 and the inflatable seal 16, depending on the size of the operative wound of a patient. The intra-operative surgical barrier 10 of the present invention may be comprised of any suitable flexible material, including but not limited to silicone, rubber/latex, polyvinyl chloride, or any combination of these materials.

Figure 1:
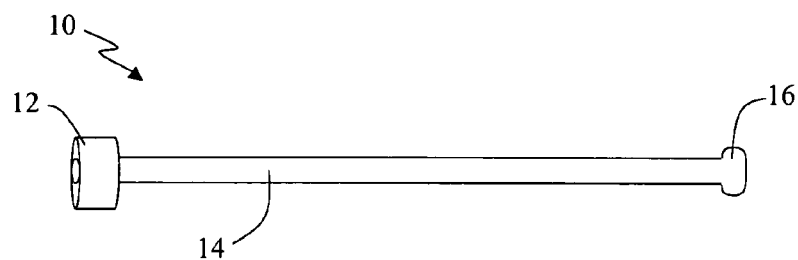
FIG. 1 is a top view of one example of a surgical barrier according to a first embodiment of present invention, shown in a deflated state.
Figure 2:
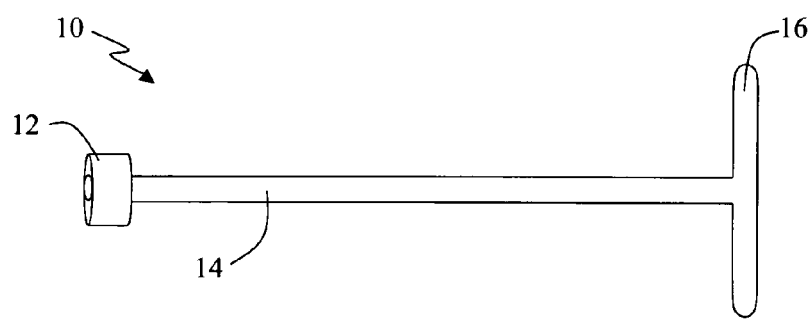
FIG. 2 is a top view of the surgical barrier of FIG. 1, shown in an inflated state.
Figure 3:
FIG. 3 is a side view of the deflated surgical barrier of FIG. 1.
Figure 4:
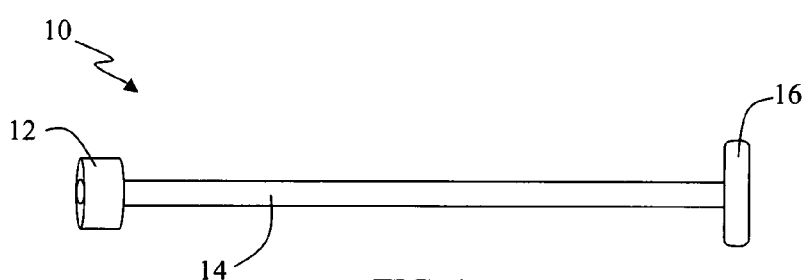
FIG. 4 is a side view of the inflated surgical barrier of FIG. 2.

In the latter stages of a surgical procedure, specifically the fusion of adjacent vertebrae using bone morphogenic protein (BMP), a surgeon or technician may introduce the surgical barrier 10 into the operative wound site in a deflated state, as illustrated in FIGS. 1 and 3. The barrier 10 may be passed through a wound site into a position adjacent to a fusion implant or cage, which contains BMP. The surgeon or technician may then attach the valve unit 12 of the barrier 10 to any sort of pressurized fluid pump, and engage the pump. This action causes the inflation fluid (typically, but not limited to, air, water, or saline) to traverse the interior lumen of the tubing 14 and enter the inflatable barrier 16. The inflatable seal 16 then expands to take the shape depicted in FIGS. 2 and 4. The expandable nature of the inflatable seal 16 serves to allow for uncomplicated introduction into the operative wound site while the seal 16 is deflated, and adequate covering of the fusion site when the seal 16 is inflated. As the seal 16 is adjacent to, and covering, the fusion implant (and thus the BMP), it provides a protective covering over the spinal fusion implant. Thus the surgeon or technician may irrigate the operative wound without fear of diluting or removing the BMP.

The external pump need only serve to provide a pressure at a level sufficient to force the inflation fluid down the tubing 14, into the seal 16, and thereafter expanding the seal 16. As such, one skilled in the art may envision any number of devices capable of performing this function, including but not limited to: a bulb-style syringe aspirator, an air compressor, or a pressurized water faucet.

The valve unit 12 serves to allow the passage of the inflation fluid from the external pump, through the tubing 14, and into the inflatable seal 16. As such, one skilled in the art may envision any of a number of shapes and structures capable of performing this function, including but not limited to: a hose clamp, regulator, needle valve, or stopcock. It is also desirable that the valve unit 12 have a cut off device to at least temporarily prevent reverse flow of the fluid, so that once the inflatable seal 16 is inflated to the proper size, the external pump may be disengaged while the seal 16 remains the proper size. That is to say, the cut off device may create a temporary one-way valve (or check-valve), so that inflation fluid may be added to the barrier 10, but not withdrawn. Then, at the conclusion of the irrigation procedure, the cut off device may be disengaged to allow the draining, deflation, and removal of the barrier 10.

The tubing 14 may be composed of any suitable water-tight flexible material, including but not limited to silicone, rubber/latex, polyvinyl chloride, or any combination of these materials. The tubing 14 may be composed in such a manner as to be flexible in movement, but less flexible in expansion, so that the fluid traverses (rather than expands) the tubing 14 causing the inflatable seal 16 to expand.

The inflatable seal 16 may be composed of any suitable water-tight flexible material, including but not limited to silicone, rubber/latex, polyvinyl chloride, or any combination of these materials. The seal 16 may be composed in such a way that, upon inflation with inflating fluid, the seal 16 has a generally rectangular shape. This may be accomplished by the lateral sides 20 expanding to create a wider seal 16 (as shown in FIG. 6), and/or the top and bottom sides 22 expanding to create a taller seal 16. It is not necessary that the thickness of the seal 16 increase, as any amount of thickness will be adequate to protect the fusion site from disruption due to irrigation. Additionally, it may be counter-productive for the thickness of the seal 16 to expand, as that itself may cause dislodgment of the fusion device or BMP.

FIGS. 5 and 6 depict one example of a structural configuration in which the inflatable seal 16 may be provided so that, upon inflation, it expands in the manner described above. As shown in the deflated state of FIG. 5, the wall thickness of the lateral sides 20 is significantly less than that of the anterior and posterior sides 24, as well as that of the tubing 14. This creates less resistance for the inflating fluid at the lateral sides 20 than at the anterior and posterior sides 24. Thus as the inflating fluid is forced into the seal 16, the lateral sides 20 expand laterally, while the anterior and posterior sides 24 generally do not expand anteriorly or posteriorly (or do so in a small amount relative to lateral expansion). FIG. 6 depicts this expanded state. Additionally, as previously disclosed, the walls of the tubing 14 should also be constructed of thicker (or entirely different, and less elastic) material, as to force the fluid into the seal 16, rather than expanding the tubing 14.

Figure 8:
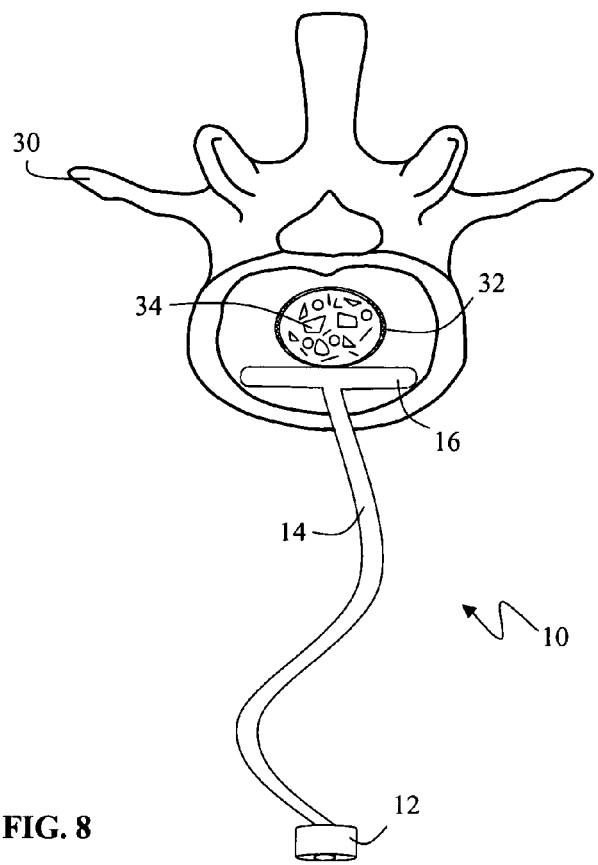

FIGS. 7 and 8 display side and top views, respectively, of one example of an in situ application of the intraoperative surgical barrier 10 of the present invention. In this instance, the barrier 10 is introduced from an anterior aspect of the spine into the intervertebral space 26 between two vertebrae 28, 30, and adjacent to a fusion implant 32. This fusion implant 32 contains BMP 34 to promote the fusion of the adjacent vertebral bodies 28, 30. Upon insertion into the proper location, the external pump fills the tubing 14, via the valve unit 12, with the inflating fluid. The fluid travels down the tubing 14 and fills the inflatable seal 16, which then inflates and expands (the stage shown in FIG. 7) to protect the fusion implant 32 and BMP 34 from dislodgement or dilution during irrigation.

Figure 9:
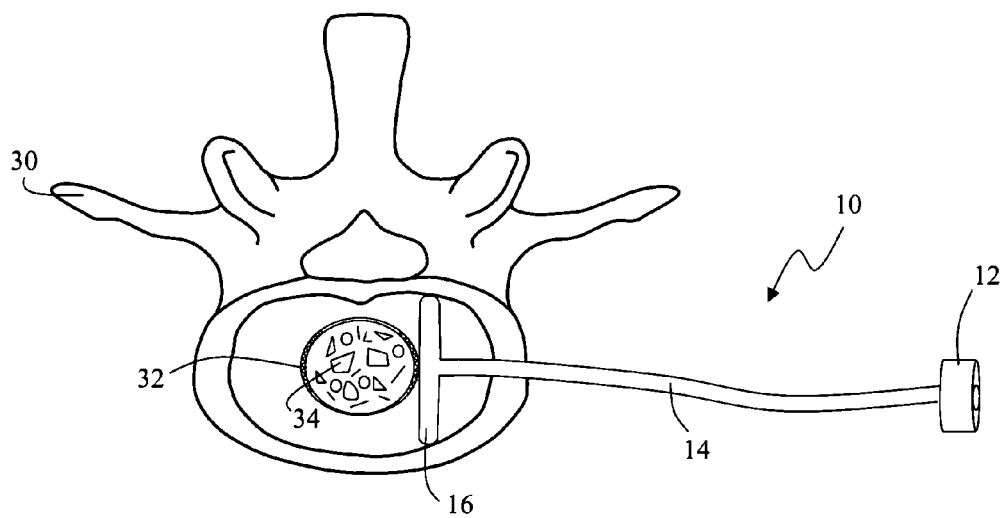
FIGS. 9-10 are top and side views, respectively, of the inflated surgical barrier of FIG. 2 applied within an intervertebral space from a lateral aspect of the spine, illustrating a second example of use according to the present invention.
Figure 10:
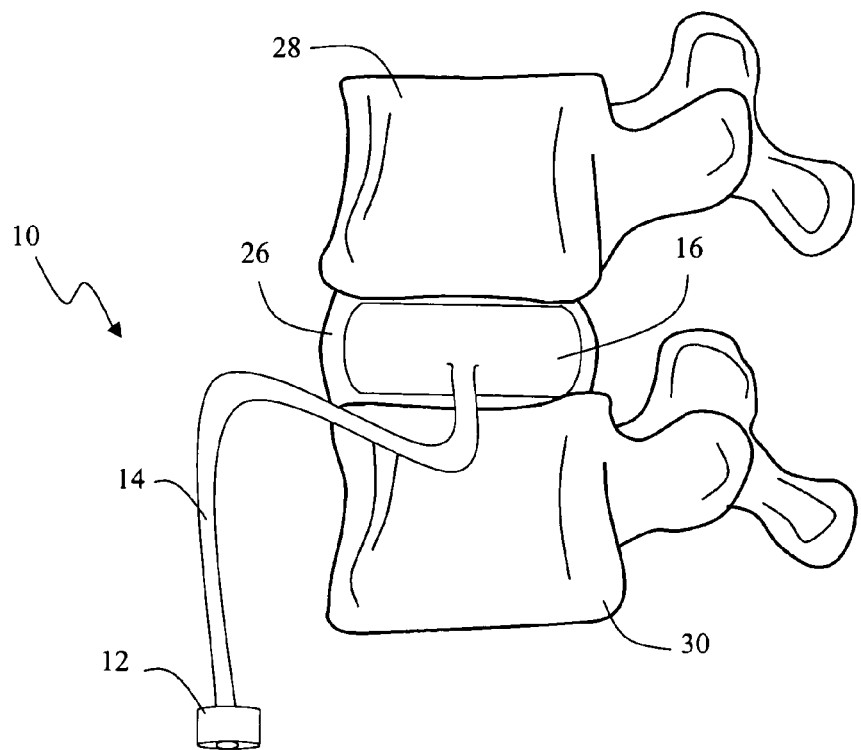

FIGS. 9 and 10 display side and top views, respectively, of a second example of an in situ application of the intraoperative surgical barrier 10 of the present invention. As spinal fusion procedures vary in entry manner (from anterior, posterior, and lateral) it is preferable that the barrier 10 be adaptable to these various procedures. In this instance, the barrier 10 is introduced from a lateral aspect of the spine (to coincide with the lateral insertion of fusion implant 32) into the intervertebral space 26 between two vertebrae 28, 30, and adjacent to fusion cage implant 32. This fusion cage implant 32 contains BMP 34 to promote the fusion of the adjacent vertebral bodies 28, 30. Upon insertion into the proper location, an external pump (not shown) fills the tubing 14, via the valve unit 12, with the inflating fluid. The fluid travels down the tubing 14 and fills the inflatable seal 16, which then inflates and expands (the stage shown in FIG. 7) to protect the fusion cage and BMP 34 from dislodgement or dilution during irrigation.

While FIGS. 7 and 8 depict the barrier 10 being introduced from an anterior aspect of the spine, and FIGS. 9 and 10 depict the barrier 10 as being introduced from a lateral aspect of the spine, it is to be appreciated that the barrier may similarly be used in any number of additional surgical techniques, including but not limited to a posterior surgical technique (e.g. PLIF) and a transforaminal surgical technique (e.g. TLIF). As such, the barrier 10 may be introduced from any aspect of the spine, including but not limited to anterior, posterior, lateral, antero-lateral, and postero-lateral.

Figure 11:
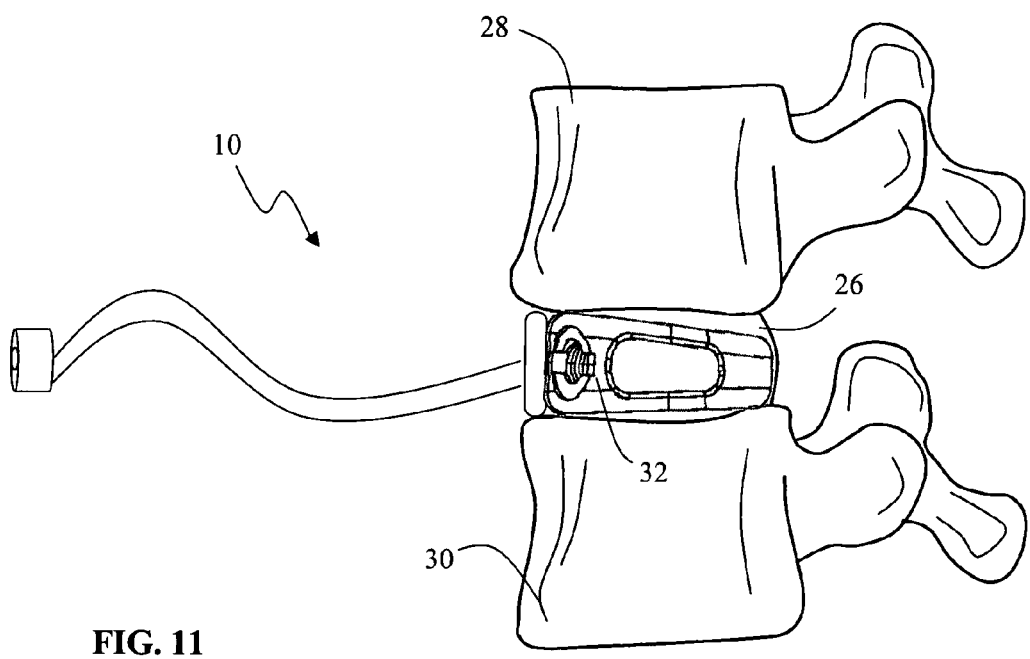
FIG. 11 is a side view of the inflated surgical barrier of FIG. 2 applied within an intervertebral space from an anterior aspect of the spine, illustrating another example of a use according to the present invention.
Figure 12:
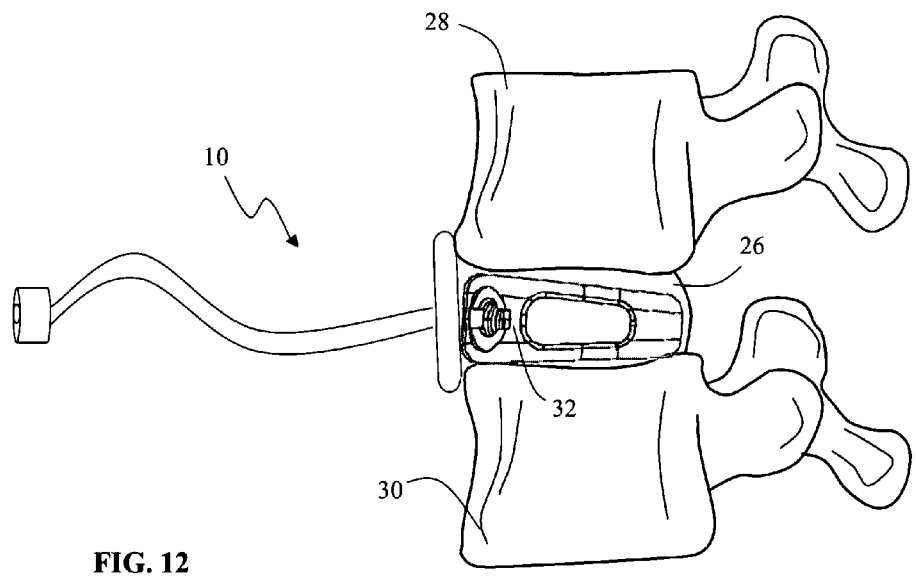
FIG. 12 is a side view of the inflated surgical barrier of FIG. 2 applied just outside an intervertebral space from an anterior aspect of the spine, illustrating another example of a use according to the present invention.

FIGS. 11 and 12 display the adaptable nature of the intraoperative surgical barrier 10 of the present invention in that the barrier may be placed within the intervertebral space 26 (FIG. 11) or outside the intervertebral space 26 and adjacent to the vertebral bodies 28, 30 (FIG. 12). This determination will be made largely in part by the size of the spinal fusion implant 32, and the particular needs of an individual operative wound. FIGS. 11 and 12 also depict the capability of the barrier 10 to adapt to the shape of the spinal fusion implant 32. The barrier 10 has a flexibility characteristic due in part to its composition material and also to the fluid nature of inflation, and thus the barrier 10 can accommodate a wide variety of shapes. As such, FIGS. 11 and 12 depict a differently shaped spinal fusion implant 32 than those found in FIGS. 7-10.

FIGS. 13-16 depict the application of an alternate embodiment of the barrier 100 of the present invention. Like the previously described embodiment of the barrier 10, the barrier 100 includes a valve unit 12, tubing 14, and an inflatable seal 102. The valve unit 12 and tubing 14 are substantially identical to that described in relation to barrier 10. The barrier 100 is composed in such a way that the inflatable seal 102 assumes a curved, or crescent, shape upon inflation. This curved shape may better approximate the shape of the vertebral bodies 105 being fused, and thus may provide better sealing capabilities.

Figure 13:
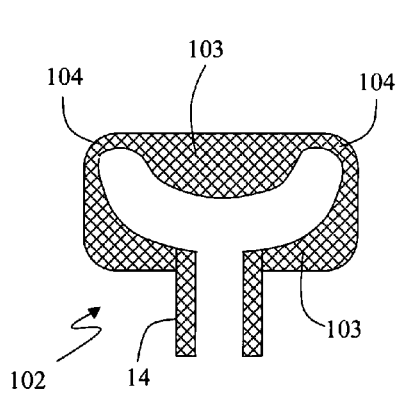
FIG. 13 is a top cross-sectional view of one example of a surgical barrier according to a second embodiment of the present invention, shown in a deflated state.
Figure 14:
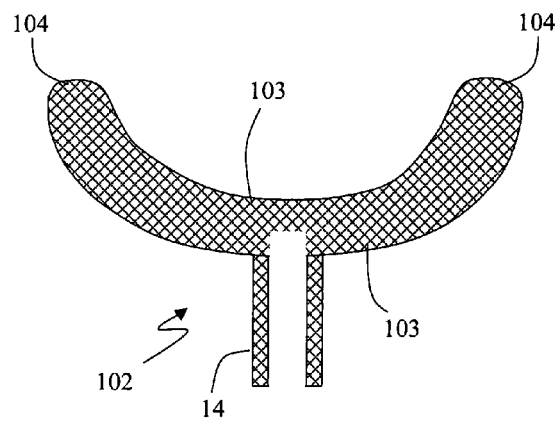
FIG. 14 is a top cross-sectional view of the surgical barrier of FIG. 13, shown in an inflated state.

As shown in FIGS. 13 and 14, this embodiment may be created by varying the thickness of the material used to compose the seal 102 so that, upon inflation, the seal 102 expands to take a curved, or crescent, shape. This can be accomplished by providing a seal with significantly thicker walls on the anterior and posterior sides 103, than on the corners 104 where expansion is to be the greatest. As such, when the inflation fluid enters the seal 102, the path of least resistance is through the corners 104, and thus the corners 104 expand to a greater degree than the thicker walls of the anterior and posterior sides 103.

Figure 15:
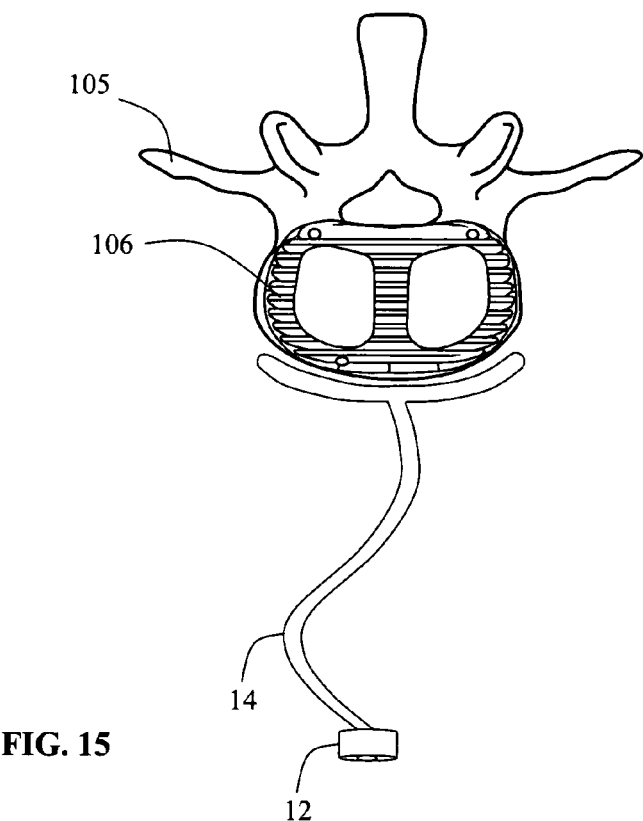
FIG. 15 is a top view of the inflated surgical barrier of FIG. 14 applied adjacent to an intervertebral space from an anterior aspect of the spine, illustrating one example of use according to the present invention.
Figure 16:
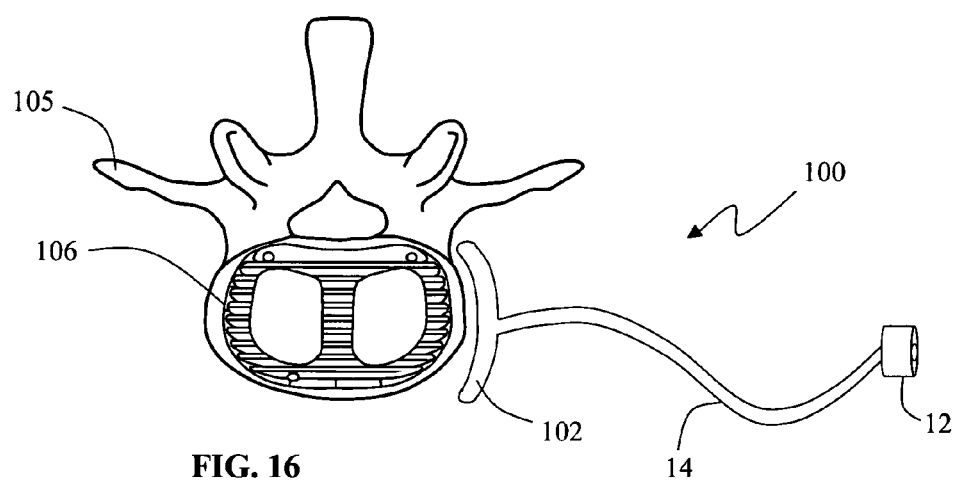
FIG. 16 is a top view of the inflated surgical barrier of FIG. 14 applied adjacent to an intervertebral space from a lateral aspect of the spine, illustrating one example of use according to the present invention.

FIG. 15 depicts this embodiment of the barrier 100 as being introduced in an anterior approach, while FIG. 16 depicts the barrier 100 as introduced from a lateral approach. Additionally, a third variety of spinal fusion implant 106 is depicted in FIGS. 15 and 16, further exemplifying the adaptability of the barrier 100 of the present invention.

Figure 17:
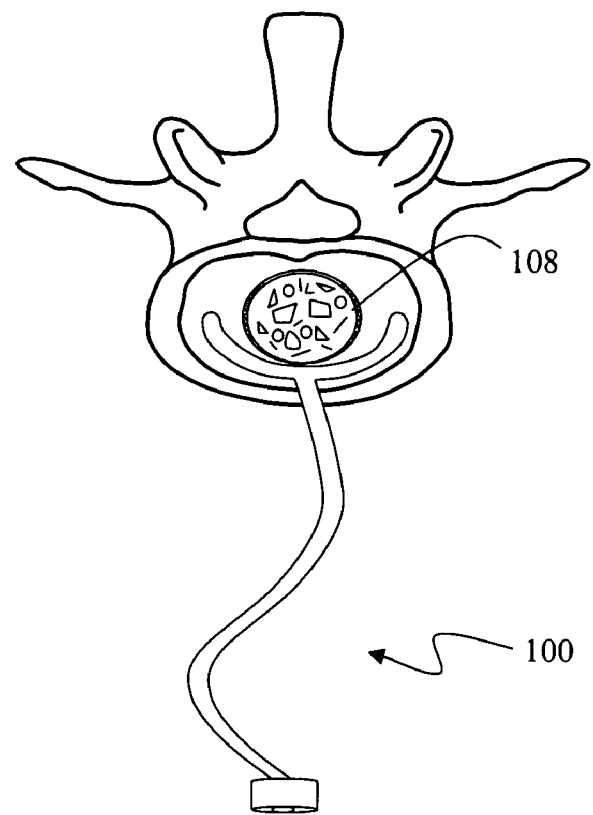
FIG. 17 is a top view of the inflated surgical barrier of FIG. 14 applied within an intervertebral space from an anterior aspect of the spine, illustrating one example of use according to the present invention.
Figure 18:
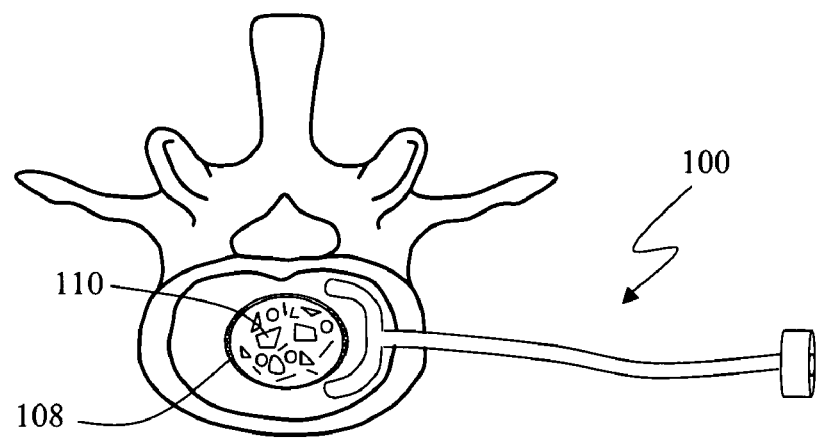
FIG. 18 is a top view of the inflated surgical barrier of FIG. 14 applied within an intervertebral space from a lateral aspect of the spine, illustrating one example of use according to the present invention.

FIGS. 17 and 18 depict the crescent-shaped embodiment of the present invention, as applied in a situation involving a smaller spinal fusion implant 108. Thus the barrier 100 may be inserted into the intervertebral space, thereby allowing the surgeon/technician to irrigate the operative wound more effectively (without disturbing the BMP 110 present in the implant 108). FIG. 17 depicts this embodiment of the barrier 100 as being introduced from an anterior approach, while FIG. 18 depicts the barrier 100 as introduced from a lateral approach. While FIGS. 15 and 17 depict the barrier 100 being introduced from an anterior aspect of the spine, and FIGS. 16 and 18 depict the barrier 100 being introduced from a lateral aspect of the spine, it is to be appreciated that the barrier 100 may be introduced from any aspect of the spine, including but not limited to anterior, posterior, lateral, antero-lateral, and postero-lateral.

Figure 19:
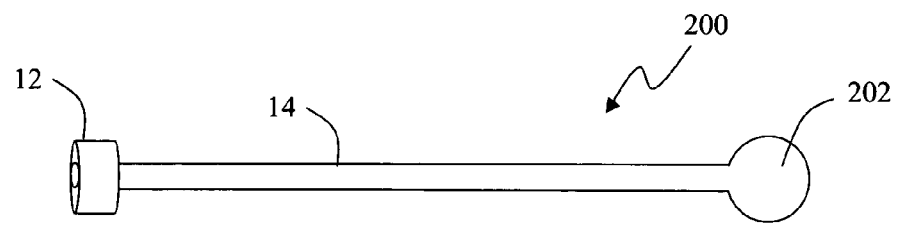
FIG. 19 is a side view of one example of a surgical barrier according to a third embodiment of the present invention, shown in an inflated state.
Figure 20:
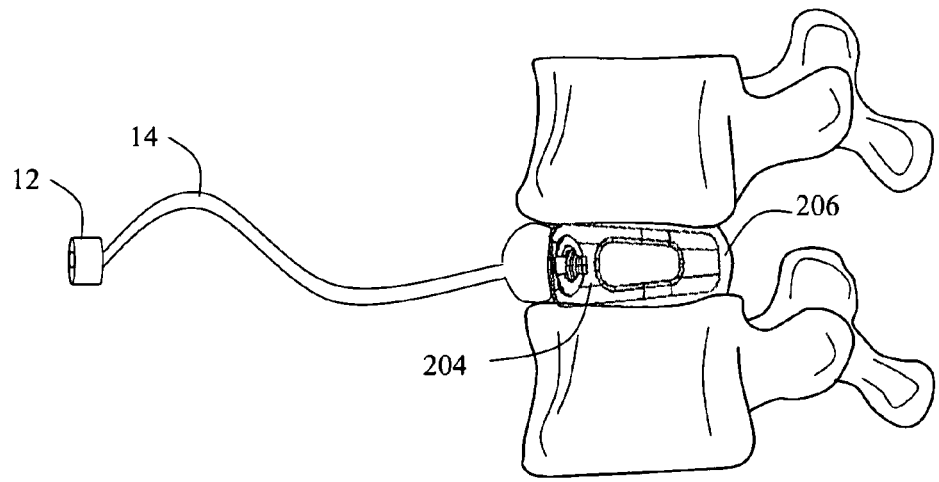
FIG. 20 is a side view of the inflated surgical barrier of FIG. 19 applied within an intervertebral space from an anterior aspect of the spine, illustrating one example of use according to the present invention.
Figure 21:
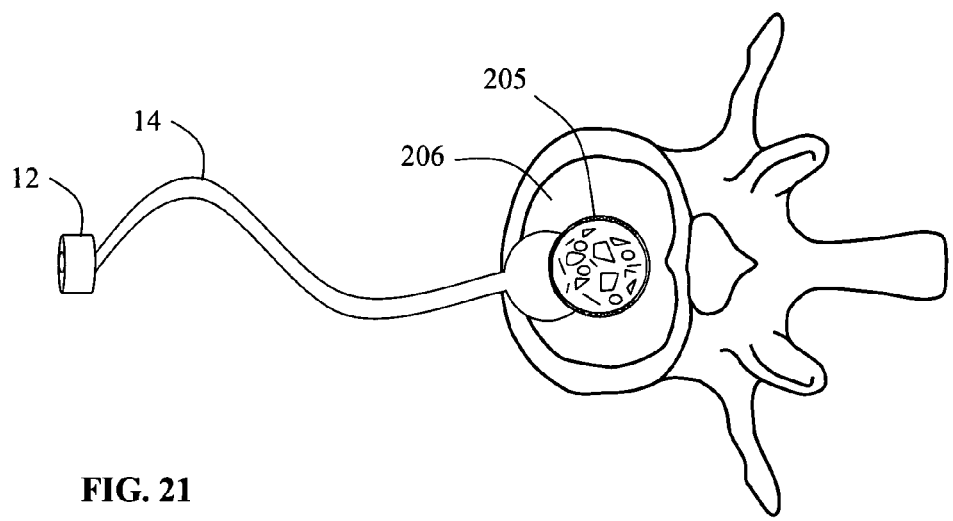
FIG. 21 is a top view of the inflated surgical barrier of FIG. 19 applied within an intervertebral space from an anterior aspect of the spine, illustrating one example of use according to the present invention.

FIGS. 19-21 depict a barrier 200 according to a third embodiment of the present invention. As with the previous embodiments, the barrier 200 includes a valve unit 12, tubing 14, and an inflatable seal 102. The valve unit 12 and tubing 14 are substantially identical to that described in relation to barrier 10. The inflatable seal 202 assumes a generally spherical shape upon inflation. As such, the barrier 200 may be inserted into a wound site and inflated, whereby the flexibility of the seal 202 allows the generally spherical shape to conform to the contours of the particular site. Thus, it may be preferable for the seal 200 to be composed in a more flexible manner (ie. through the use of different materials, or by creating thinner walls) to allow the seal 200 to conform to the shape of the target site. Both FIG. 20 and FIG. 21 depict the entry of the barrier 200 from an anterior aspect of the spine. The figures differ however in the size and shape of the spinal fusion implants 204, 205 inserted into the intervertebral space 206. FIG. 20 depicts a larger implant 204, and thus the barrier 200 may be disposed outside the intervertebral space 206, while FIG. 21 depicts a smaller fusion implant 205, and thus the barrier 200 may be disposed within the intervertebral space 206 during irrigation. While FIGS. 19-21 depict the barrier 200 being introduced from an anterior aspect of the spine, it is to be appreciated that the barrier 200 may be introduced from any aspect of the spine, including but not limited to anterior, posterior, lateral, antero-lateral, and postero-lateral.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. For instance, although the preferred embodiments described herein describe an intraoperative surgical barrier for use during spinal fusion procedures, it is apparent that the device may be used in any surgical technique where a particular region of a patient's anatomy must be separated from the general operative environment.

What is claimed is:

1. A method of fusing a first vertebral body to a second vertebral body, the first and second vertebral bodies separated by an intervertebral space, comprising:

establishing an operative corridor to a surgical target site, the surgical target site including the intervertebral space and at least a portion of the first and second vertebral bodies;

introducing a fusion implant into the intervertebral space through said operative corridor, the fusion implant including fusion-enhancing material;

introducing at least a portion of an intraoperative surgical barrier through the operative corridor to the surgical target site, the intraoperative surgical barrier including an elongated flexible tube member comprising first and second opposing ends separated by an elongated body portion, the tube member having a lumen dimensioned to allow traversal of a fluid therethrough, a valve unit in fluid communication with the lumen of the elongated flexible tube member and adapted to communicate with a pressurized fluid pump, and an expandable seal member provided at the second end of the elongated flexible tube member;

expanding the expandable seal member to establish a barrier between the fusion implant and at least a portion of the surgical target site and the operative corridor, wherein the expandable seal member has a shape comprising at least one of generally rectangular, generally spherical, and generally crescent-shaped;

irrigating the surgical target site after introduction of the intraoperative surgical barrier and expansion of the expandable seal member; and removing the intraoperative surgical barrier from the surgical target site and the operative corridor.

2. The method of claim 1, wherein the expandable seal member is introduced into the intervertebral space prior to the step of expanding the expandable seal member.

3. The method of claim 1, wherein at least one of the elongated flexible tube member and the inflatable seal are made from at least one of silicone, rubber, latex, polyvinyl chloride, and any combination of silicone, rubber, latex, and polyvinyl chloride.

4. The method of claim 1, wherein the operative corridor is established from an approach to the spine comprising at least one of anterior, posterior, lateral, antero-lateral, and postero-lateral.

5. The method of claim 1, wherein the fusion-enhancing material is bone morphogenic protein.

* * * * *